United States Patent [19]

Senet et al.

[11] Patent Number: 4,970,319

[45] Date of Patent: Nov. 13, 1990

[54] PROCESS FOR THE PREPARATION OF ACYL ISOCYANATES

[75] Inventors: Jean-Pierre Senet, La Chapelle La Reine; Serge Lecolier, Janville Sur Juine; Paul Caubere, Nancy, all of France; Deng Min-Zhi, Shanghai, China

[73] Assignee: Societe Nationale Des Poudres Et Explosifs, Paris, France

[21] Appl. No.: 327,529

[22] Filed: Mar. 23, 1989

[30] Foreign Application Priority Data

Mar. 25, 1988 [FR] France ................................ 88 03915

[51] Int. Cl.⁵ .................. C07D 213/78; C07D 305/10; C07D 333/38; C07C 263/02
[52] U.S. Cl. .................................... 546/316; 562/871; 549/72; 549/487; 558/415
[58] Field of Search ........................ 562/871; 546/316; 594/72, 487; 558/415

[56] References Cited

U.S. PATENT DOCUMENTS 3,155,700 11/1964 Steyermark et al. ................ 562/871
3,450,747 6/1969 Smith et al. ......................... 562/871
3,850,985 11/1974 Hagemann .......................... 562/871
4,529,919 7/1985 Clifford et al. ..................... 546/290

OTHER PUBLICATIONS

Anhydrous aluminum Choride in Organic Chemistry, C. A. Thomas, 1941, pp. 156-157, 381, 531, 596, 602, 636-644.

Synthetic Methods of Organic Chemistry, W. Theilheimer, 1972, 26/687, p. 334.

Chemical Communication, H. H. Wasserman and S. H. Wentland, 1969, p. 1216.

Primary Examiner—Mary C. Lee
Assistant Examiner—Joseph K. McKane
Attorney, Agent, or Firm—Bucknam and Archer

[57] ABSTRACT

The invention relates to a process for the preparation of acyl isocyanates of formula

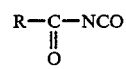

in which R is an alkyl radical, a substituted or unsubstituted naphthyl or phenyl radical or a substituted or unsubstituted aromatic heterocyclic radical, which consists in reacting an acyl halide of formula

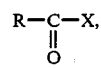

in which R has the above meaning and X denotes a fluorine, chlorine or bromine atom, with a sodium or potassium cyanate in the presence of a compound chosen from tin(IV), zinc or nickel(II) halides.

The acyl isocyanates thus prepared are very useful for forming ureas or carbamates.

9 Claims, No Drawings

PROCESS FOR THE PREPARATION OF ACYL ISOCYANATES

The invention relates to a new process for the preparation of acyl isocyanates from acyl halides.

Acyl isocyanates are intermediates which are highly useful for the preparation of ureas, carbamates and polymers.

Some processes have been proposed for preparing these isocyanates.

One of these processes consists in reacting an acyl halide with a silver cyanate (Hill and Degnan, J. Am. Chem. Soc. (1940) 62 p. 1595–1596). Unfortunately, silver cyanate is a very costly reactant, and the process cannot be employed industrially.

According to another process (U.S. Pat. No. 3,155,700), a acyl halide is reacted with isocyanate acid in the presence of a weak base such as a tertiary amine.

However, isocyanic acid is very unstable (cf. Traité de Chimie Organique V. Grignard XIV (1949) p. 172). It is not a commercial product and it is very difficult to prepare, so that the use of this process on a large scale is not possible.

Another process (U.S. Pat. No. 4,529,819) consists in reacting a benzoyl chloride with an alkali metal cyanate in the presence of cuprous chloride, but the yields obtained are low and do not exceed 50%.

There has accordingly been a great need for an economical process for the preparation of acyl isocyanates.

The subject matter of the present invention is a process of preparation which does not exhibit the disadvantages of the previous processes and which makes it possible to obtain many acyl isocyanates in a very good yield, in a simple manner and from inexpensive compounds.

More particularly, the present invention relates to a process for the preparation of acyl isocyanates of formula

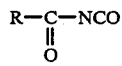

in which

R denotes a linear or branched $C_1$–$C_4$ alkyl radical, a phenyl or naphthyl radical carrying groups $R^1$, $R^2$ and $R^3$, $R^1$ denoting a hydrogen, fluorine, chlorine or bromine atom, or a $C_1$–$C_4$ alkyl, $C_1$–$C_4$ haloalkyl, $C_1$–$C_4$ alkoxy or $C_1$–$C_4$ fluoro- or chloroalkoxy radical, denoting a hydrogen, fluorine, chlorine or bromine atom or a $C_1$–$C_4$ alkyl, $C_1$–$C_4$ haloalkyl, $1$–$C_4$ alkoxy or $C_1$–$C_4$ fluoro- or chloroalkoxy radical, and $R_3$ denoting a hydrogen, fluorine, chlorine or bromine atom, or a $C_1$–$C_4$ alkyl or $C_1$–$C_4$ haloalkyl radical, a nitro or cyano group, or denoting an aryloxy radical when it is not attached to a carbon neighbouring the carbon bonded to

functional group,
-a five- or six-membered aromatic heterocyclic radical carrying or not carrying substituents chosen from $C_1$–$C_4$ alkyl radicals and fluorine, chlorine or bromine atoms, the heteroatom(s) being chosen from oxygen, sulphur or nitrogen atoms, which consists in reacting an acyl halide of the formula

in which R has the above meaning and X denotes a fluorine chlorine or bromine atom with sodium or potassium cyanate in an inert solvent in the presence of at least one compound chosen from tin(IV), zinc or nickel-(II) halides. In the present application and in the claims the term "haloalkyls" denotes alkyl radicals containing from 1 to 5 fluorine, chlorine or bromine atoms. The reaction may be represented by the following equation:

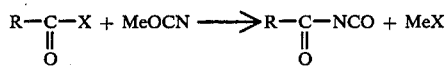

In the formulae, R and X have the above meanings and Me denotes sodium or potassium.

The acyl halides employed as starting compounds in the process according to the invention are compounds which are to be found in commerce, or which can be easily prepared according to known processes (Houben Weyl, Methoden der Organischen Chemie (1985) E.5/1 p. to 609).

For economy reasons, acyl chlorides are generally employed.

By way of examples of acyl halides which can be employed as starting compounds there may be mentioned halides in which R is a methyl or ethyl radical, such as acetyl and propionyl chlorides, the halides in which R is a phenyl or naphthyl radical carrying the groups $R^1$, $R^2$ and $R^3$, $R^1$ denoting a hydrogen, fluorine or chlorine atom, a $C_1$–$C_2$ alkyl or $C_1$–$C_2$ alkoxy radical or the $CF_3$, $CCl_3$, $CBr_3$ or $OCF_3$ radicl, and $R^3$ denoting a hydrogen, fluorine or chlorine atom, a $C_1$–$C_2$ alkyl radical or the $CF_3$, $CCl_3$ or $CBr_3$ radical, or, when it is not attached to a carbon neighbouring the carbon bonded to the

phenoxy radical, such as o-chloro-, m-chloro-, p-chloro-, o-methyl-, m-methyl-, p-methyl-, p-trifluoromethyl-, o-methoxy-, m-methoxy-, p-methoxy-, m-nitro-, p-nitro, 2,6-dichloro-, 2,6-difluoro-, p-phenoxy benzoyl fluorides, chlorides or bromides, and the halides in which R is a furyl, thienyl or pyridyl radical.

The acyl halide is reacted with sodium or potassium cyanate, for economic reasons preferably with sodium cyanate. The quantities are generally close to stoichiometry. A slight excess of cyanate is preferably employed.

The reaction must be carried out in the presence of at least one nickel(II) tin(IV) or zinc halide. The term halide denotes a fluoride, chloride, bromide or iodide.

It has been found, in fact, that in the absence of these halides or in the presence of other metal halides, such as those of iron, titanium and aluminium, the acyl isocyanates are not formed.

With nickel(II) and zinc halides, in particular with the chlorides, the yields are good. They are markedly better with tin(IV) halides and in particular with tin(IV) chloride, which is the preferred compound.

The quantity of metal halide is not critical. It must not be too low nor too high if good yields are to be obtained. It is generally between 1 and 10%, preferably between 2 and 6%, on a molar basis, relative to the starting acyl halide.

The compounds are dissolved or suspended in a preferably anhydrous solvent medium. The solvent employed may be a halogenated aromatic solvent such as chlorobenzene or o-dichlorobenzene, trichloroethylene, glyme, diglyme, dioxane, or a mixture of acetonitrile and of a nonpolar solvent such as benzene or carbon tetrachloride, for example in a ratio of 45:55.

o-Dichlorobenzene is preferably employed.

The reaction temperature is generally between 75° and 200° C.

The reflux temperature is preferably chosen, particularly when the starting compounds are aromatic acyl halides.

Since the presence of water in the reaction medium can cause secondary reactions and reduce the yield of isocyanates, the reaction is preferably carried out under practically anhydrous conditions. The compounds are generally reacted in an inert atmosphere.

A particular embodiment of the invention consists in reacting the compounds, for example under nitrogen or argon, in stirring the reaction mixture for a few hours at the chosen temperature and in then recovering the acyl isocyanate after filtration and distillation.

The present process makes it possible to obtain, in an excellent yield, many acyl isocyanates which can easily react in a known manner with many compounds, for example amines, alcohols or phenols, to form ureas and carbamates which are particularly useful as plant protection products or as medications (cf. for example, CA 90:71932z, 90:152238e, 91:5028d, 63:15250h).

The examples which follow illustrate the invention without, however, limiting it in any way.

EXAMPLES 1 to 17

Various aromatic or heteroaromatic acyl chlorides have been employed in these examples. General operating procedure. The acyl chloride (1 mol) dissolved in 200 ml of dried o-dichlorobenzene and SnCl$_4$ (0.05 mol) was added with stirring and under an argon atmosphere to a suspension of NaOCN (1.3 mol) in 200 ml of o-dichlorobenzene.

The mixture was stirred for two hours at reflux temperature (180° C.), was cooled to ambient temperature and was filtered under argon. The filtrate was then distilled under reduced pressure to obtain the acyl isocyanate.

The results are collated in Table I.

TABLE I

| EX NUMBER | R | B.p (°C.) mm Hg | YIELD (%) |
|---|---|---|---|
| 1 |  | 74–76 10 mm | 83 |
| 2 | 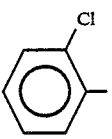 | 98–101 2 mm | 80 |
| 3 | 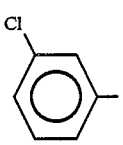 | 103–107 5 mm | 81 |
| 4 | 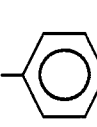 | 92–95 2 mm | 85 |
| 5 | 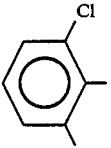 | 123–126 1–1.5 mm | 87 |
| 6 | 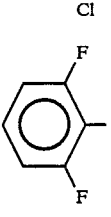 | 83–88 9–10 mm | 70 |
| 7 | 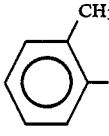 | (183–184)* | (85)** |
| 8 | 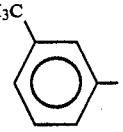 | 84–86 2 mm | 80 |
| 9 | 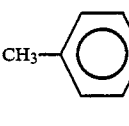 | 82–84 1.6 mm | 81 |
| 10 | 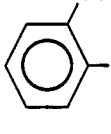 | 115–117 1 mm | 67 |
| 11 |  | 104–107 2 mm | 78 |

TABLE I-continued

| EX NUMBER | R | B.p (°C.) mm Hg | YIELD (%) |
|---|---|---|---|
| 12 | CH₃O—⟨phenyl⟩— | (200-201)* | (73)** |
| 13 | ⟨phenyl⟩—O—⟨phenyl⟩— | 131-135 0.5-0.7 mm | 76 |
| 14 | 2-O₂N-⟨phenyl⟩— | 103-107 0.5 mm | 78 |
| 15 | 4-O₂N-⟨phenyl⟩— | 120-123 1.5 mm | 84 |
| 16 | 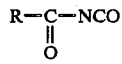 | 80-83 15 mm | 71 |
| 17 | 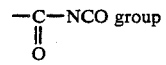 | □ | 80 |

*The figure in brackets shows the melting point of the urea obtained by reaction of the isocyanate formed with one mole of aniline.
**The figure in brackets shows the yield of urea.
□IR spectrum: ν (N═C═O) = 2240 cm⁻¹

EXAMPLE 18

The operating procedure is the same as in example 6, but the 2,6-difluorobenzoyl chloride is replaced with the 2,6-difluorobenzoyl fluoride. The 2,6-difluorobenzoyl isocyanate is obtained with a yield of 75%. B.p.:78° C.-80° C. under 0.5 mm Hg.

EXAMPLES 19 and 20

In these examples the acyl chlorides employed are aliphatic acyl chlorides. Operating procedure The acyl chloride (1 mol) dissolved in 75 ml of dried o-dichlorobenzene and SnCl₄ (0.05 mol) was added with stirring and under an argon atmosphere to a suspension of NaOCN (1.3 mol) in 75 ml of dried o-dichlorobenzene.

The mixture was stirred at 80° C. for 8 hours and filtered under argon. The filtrate was then distilled under nitrogen to obtain the acyl isocyanate. The results are collated in Table II.

TABLE II

| EX NUMBER | R | B.p. (°C.) mm Hg | YIELD (%) |
|---|---|---|---|
| 19 | CH₃— | 78-80 | 36 |
| 20 | CH₃CH₂— | 96-98 | 52 |

EXAMPLE 21

Benzoyl chloride (0.2 mol) dissolved in 100 ml of dried CH₃CN and 125 ml of dried C₆H₆ and 0.01 mole of ZnCl₂ were added with stirring and under argon to a suspension of 0.26 mol of NaOCN in 100 ml of dried CH₃CN and 125 ml of dried C₆H₆. The mixture was stirred at the reflux temperature (78° C.) for 8 hours and was then cooled to ambient temperature. Without isolating the benzoyl isocyanate, benzylamine (0.2 mol) dissolved in 100 ml of C₆H₆ was added dropwise to the mixture at ambient temperature. The mixture was stirred for half an hour and 1000 ml of water were then added to dissolve the salts. The mixture obtained was filtered and the urea of formula C₆H₅CONH-CONHCH₂C₆H₅ was recovered in the form of a white solid which was recrystallized from ethanol (36.1 g, 71% yield), melting point 166° C.

COMPARATIVE EXAMPLES 1 to 4

The operating procedure employed was the same as in Example 21, but
in comparative Example 1 no metal halide was added,
in comparative Example 2 ZnCl₂ was replaced with FeCl₃,
in comparative Example 3 ZnCl₂ was replaced with TiCl₄,
in comparative Example 4 ZnCl₂ was replaced with AlCl₃.

In all these examples, no reaction between cyanate and the benzoyl chloride was observed, and the latter was recovered almost entirely in the form of N-benzylbenzamide.

We claim:
1. A process for the preparation of acyl isocyanates of formula

$$R-\underset{\underset{O}{\|}}{C}-NCO$$

wherein R is
methyl or ethyl; phenyl or naphthyl carrying the groups R¹, R² and R³, wherein R¹ is hydrogen, fluorine, chlorine, C₁-C₂ alkyl, C₁-C₂ alkoxy, CF₃, CCl₃, CBr₃ or OCF₃, R² is hydrogen, fluorine, chlorine, C₁-C₂ alkyl, C₁-C₂ alkoxy, CF₃, CCl₃, CBr₃, or OCF₃, R³ is hydrogen, fluorine, chlorine, C₁-C₂ alkyl, CF₃, CCl₃, CBr₃ or when it is not attached to a carbon neighboring the carbon bonded to the $$-\underset{\underset{O}{\|}}{C}-NCO \text{ group}$$

nitro or phenoxy,
a furyl, thienyl or pyridyl; which consists of reacting an acyl halide of formula $$R-\underset{\underset{O}{\|}}{C}-X$$

wherein R has the above meaning and X is fluorine, chlorine or bromine with a sodium or potassium cyanate in an inert solvent in the presence of at least one compound which is a tin (IV), zinc or nickel (II) halide.

2. Process according to claim 1, characterized in that X denotes chlorine.

3. Process according to claim 1 characterized in that sodium cyanate is employed.

4. Process according to claim 1 characterized in that the solvent is a halogenated aromatic solvent, an acetonitrile-nonpolar solvent mixture, trichloroethylene, glyme, diglyme or dioxane.

5. Process according to claim 4, characterized in that the solvent is p-dichlorobenzene.

6. Process according to claim 11 characterized in that the metal halide is a chloride.

7. Process according to claim 6, characterized in that tin(IV) chloride is employed.

8. Process according to claim 1, characterized in the metal halide is employed in a quantity of between 1 and 10 mol% relative to the acyl halide, preferably between 2 and 6 mol%.

9. Process according to claim 1 characterized in that the reaction is carried out at a temperature of between 75° and 200° C.

* * * * *

UNITED STATES PATENT AND TRADEMARK OFFICE
CERTIFICATE OF CORRECTION

PATENT NO. : 4,970,319
DATED : November 13, 1990
INVENTOR(S) : Jean-Pierre Senet, et al It is certified that error appears in the above-identified patent and that said Letters Patent is hereby corrected as shown below:

Column 1, line 52: should read as follows: --

$R_2$ denoting a hydrogen, fluorine, chlorine or bromine --

Column 1, line 53: should read as follows: -- atom or a $C_1$-$C_4$ alkyl, $C_1$-$C_4$ haloalkyl, $C_1$-$C_4$ --

Column 2, line 45: after "$OCF_3$ radical" insert: --

$R^2$ denoting a hydrogen, fluorine or chlorine atom, a $C_1$-$C_2$ alkyl or $C_1$-$C_2$ alkoxy radical or the $CF_3$, $CCl_3$, $CBr_3$ or $OCF_3$ radical --

Column 2, line 55: before "phenoxy radical" insert: -- a nitro group or --

Signed and Sealed this

Sixth Day of October, 1992

*Attest:*

DOUGLAS B. COMER

*Attesting Officer*      *Acting Commissioner of Patents and Trademarks*